(12) United States Patent
Basheer et al.

(10) Patent No.: US 10,324,012 B2
(45) Date of Patent: Jun. 18, 2019

(54) METHOD FOR DETECTING AND QUANTIFYING HALOETHER CONTAMINATION IN AQUEOUS SAMPLES BY FLOW ASSISTED ELECTRO-ENHANCED SOLID-PHASE MICROEXTRACTION

(71) Applicant: KING FAHD UNIVERSITY OF PETROLEUM AND MINERALS, Dhahran (SA)

(72) Inventors: Chanbasha Basheer, Dhahran (SA); Abdulnaser Khaled Alsharaa, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 711 days.

(21) Appl. No.: 14/989,476

(22) Filed: Jan. 6, 2016

(65) Prior Publication Data

US 2017/0052153 A1    Feb. 23, 2017

Related U.S. Application Data

(60) Provisional application No. 62/207,771, filed on Aug. 20, 2015.

(51) Int. Cl.
*G01N 1/40* (2006.01)
*G01N 30/06* (2006.01)
(Continued)

(52) U.S. Cl.
CPC .......... *G01N 1/40* (2013.01); *G01N 30/482* (2013.01); *G01N 27/447* (2013.01);
(Continued)

(58) Field of Classification Search
None
See application file for complete search history.

(56) References Cited

U.S. PATENT DOCUMENTS 8,598,325 B2    12/2013    Pawliszyn

FOREIGN PATENT DOCUMENTS

| CN | 102636595 A | 8/2012 |
| CN | 102879255 A | 1/2013 |

OTHER PUBLICATIONS

Amayreh, M.Y. "Development of automated on-site analytical methods for water analysis," King Fahid University of Petroleum and Minerals (Saudi Arabia), ProQuest Dissertations Publishing, 2013. 10186483. (Year: 2013).*

(Continued)

*Primary Examiner* — Christopher Adam Hixson
*Assistant Examiner* — Michelle Adams
(74) *Attorney, Agent, or Firm* — Oblon, McClelland, Maier & Neustadt, L.L.P.

(57) ABSTRACT

A method for detecting and quantifying haloether contamination in aqueous samples. A flow state is artificially induced upon an aqueous sample and a solid phase microextraction (SPME) fiber, upon which an electric potential is applied, is exposed to the flowing aqueous sample in direct immersion mode. Halide ions liberated from electrophoretically dehalogenated haloether compounds contained in the aqueous sample are absorbed upon the SPME fiber, then later desorbed at a gas chromatograph, separated into individual halide ions and analyzed by mass spectrometry. Effects of various parameters such as absorption time, sample pH, salt content, applied voltage, SPME fiber type, flow rate and background matrix are also described.

17 Claims, 8 Drawing Sheets

(51) Int. Cl.
*B01J 20/281* (2006.01)
*G01N 27/447* (2006.01)
*G01N 30/88* (2006.01)

(52) U.S. Cl.
CPC ............... *G01N 2001/4038* (2013.01); *G01N 2030/062* (2013.01); *G01N 2030/884* (2013.01); *Y10T 436/193333* (2015.01)

(56) References Cited

OTHER PUBLICATIONS

Alsharaa, A. et al. "Flow-Assisted Electro-Enhanced Solid-Phase Microextraction for the Determination of Haloethers in Water Samples," Chromatographia (2016) 79:97-102. First Online: Dec. 9, 2015. (Year: 2015).*

Xu, R. et al. "Application of electro-enhanced solid phase microextraction combined with gas chromatography—mass spectrometry for the determination of tricyclic antidepressants in environmental water samples," Journal of Chromatography A, 1350 (2014) 15-22. (Year: 2014).*

Mousa, A. et al. "Application of electro-enhanced solid-phase microextraction for determination of phthalate esters and bisphenol A in blood and seawater samples," Talanta 115 (2013) 308-313. (Year: 2013).*

Cai, Q.-Y. "Occurrence of organic contaminants in sewage sludges from eleven wastewater treatment plants, China," Chemosphere vol. 68, Issue 9, Aug. 2007, pp. 1751-1762 (Year: 2007).*

Mousa, A. et al. "Flow-assisted automated solid-phase microextraction for the determination of chloroethers in aqueous matrices," Intern. J. Environ. Anal. Chem. vol. 95, No. 8, pp. 744-753; Published online: Jun. 12, 2015 (Year: 2015).*

Xiaolan Chai, et al., "Electrosorption-enhanced solid-phase microextraction using activated carbon fiber for determination of aniline in water", Journal of Chromatography A, vol. 1165, Issues 1-2, Sep. 21, 2007, pp. 26-31 (with Abstract).

Ruyi Xu, et al, "Application of electro-enhanced solid phase microextraction combined with gas chromatography—mass spectrometry for the determination of tricyclic antidepressants in environmental water samples", Journal of Chromatography A, vol. 1350, Jul. 11, 2014, pp. 15-22 (Abstract only).

* cited by examiner

METHOD FOR DETECTING AND QUANTIFYING HALOETHER CONTAMINATION IN AQUEOUS SAMPLES BY FLOW ASSISTED ELECTRO-ENHANCED SOLID-PHASE MICROEXTRACTION

CROSS-REFERENCE TO RELATED APPLICATIONS

This application claims the benefit of U.S. Provisional Application Ser. No. 62/207,771, filed Aug. 20, 2015, the entire contents of which are incorporated herein by reference.

STATEMENT OF FUNDING ACKNOWLEDGEMENT

This project was funded by the National Plan for Science, Technology and Innovation (NSTIP)—King Abdulaziz City for Science and Technology—the Kingdom of Saudi Arabia, award number (10-WAT1396-04).

BACKGROUND OF THE INVENTION

Technical Field

The present invention relates to a method in analytical chemistry. More specifically, the present invention relates a method for detecting and determining the concentration of one or more haloether compounds in an aqueous sample by solid phase microextraction and gas chromatography-mass spectrometry techniques.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Haloethers are compounds which contain an ether moiety (R—O—R) and halogen atoms attached to the aryl or alkyl groups. Haloethers are a class of disinfection by-products (DBPs) that are unintentionally produced from the reactions of disinfectants with organic matter naturally present in the water [Richardson, S. D., 2009. Water Analysis: Emerging Contaminants and Current Issues. Analytical Chemistry, 81, 4645—incorporated herein by reference in its entirety]. They are harmful to humans and have been shown to be carcinogenic even at low parts per billion (ppb) levels. In addition to that haloethers are widely used in industry as solvents for fiber processing, polymers, pesticides, medicine, and ion exchange resins and thereby enter into the aqueous environment [Chiing. C. C., Ren. J. W., Chun, Y., Chung. S. L., 2009. Bis (2-chloroethoxy) methane degradation by $TiO_2$ photocatalysis: parameter and reaction pathway investigations. J. Hazard. Mater 172, 1021; Jing. S. C., Shang. D. H., 2007. Determination of haloethers in water with dynamic hollow fiber liquid-phase microextraction using GC-FID and GC-ECD. Talanta 71, 882; Montgomery and Welkom 1990. Montgomery, J. H., Welkom, L. M., 1990. Groundwater Chemical Desk Reference, Lewis Publishers, Chelsea, Mich.; Thomas, O. V., Stork, J. R., Lammert, S. L., 1980. The chromatographic and GC/MS analysis of organic priority pollutants in water. J. Chromatogr. Sci. 18, 58—each incorporated herein by reference in its entirety]. Haloethers are persistent contaminants and are of great concern because of their carcinogenicity and toxicity [Sittig, M., 1991. Handbook of Toxic and Hazardous Chemicals and Carcinogens, third ed., Noyes Public, New Jersey; Shang, D. H., Yi, T. C., Cheng. S. L., 1997. Determination of haloethers in water by solid-phase microextraction. J. Chromatogr. A 769, 239; Fawell, J. K., Hunt, S., 1988. Environmental Toxicology: Organic Pollutants, Wiley, New York, (Chapter 9); Wennrich, L., Engewald, W., Poppb, P., 1997. Determination of chloroethers in aqueous samples using solid-phase microextraction. Acta Hydrochim. Hydrobiol. 25, 329—each incorporated herein by reference in its entirety].

In 1979, the United States Environmental Protection Agency (USEPA) classified five Haloethers as priority pollutants, and proposed a maximum allowed contaminant level (MCL) of 500 µg/L [USEPA 1980. United States Environmental Protection Agency, Office of Water Regulations and Standards Criteria and Standards Division Washington D.C. 20460 440/5-80-050 October 1980—incorporated herein by reference in its entirety]. 4-chlorophenyl phenyl ether (CPPE) and 4-bromophenyl phenyl ether (BPPE) are among these priority haloethers, and their chemical structures are shown in FIGS. 1A and 1B. The physical properties of CPPE and BPPE are listed in Table 1.

TABLE 1

Physical properties of CPPE and BPPE.

| Physical properties | CPPE | BPPE |
|---|---|---|
| Molecular weight (g $mol^{-1}$) | 204.6 | 249.1 |
| Solubility at 20-25° C. (mg $L^{-1}$) | 1.43 | 0.82 |
| Boiling point (° C.) | 161 | 305 |
| Vapor pressure at 20-25° C. (mmHg) | 0.0016 | 0.0005 |
| Henry's law constant at 20° C. | 0.012 | 0.009 |
| Diffusion coefficient in air ($cm^2$ $s^{-1}$) | 0.048 | 0.047 |
| Diffusion coefficient in water ($cm^2$ $s^{-1}$) | 6.18E−06 | 6.27E−06 |

USEPA methods 611 and 625 that are based on liquid-liquid extraction (LLE) were established to determine haloethers from aqueous samples [Thomas, O. V., Stork, J. R., Lammert, S. L., 1980. The chromatographic and GC/MS analysis of organic priority pollutants in water. J. Chromatogr. Sci. 18, 583; Shang, D. H., Yi, T. C., Cheng. S. L., 1997. Determination of haloethers in water by solid-phase microextraction. J. Chromatogr. A 769, 239—each incorporated herein by reference in its entirety]. However, these techniques require hazardous solvents, multi-step and time-consuming extraction procedures, and the risk of haloether loss in extraction and concentration steps [Wennrich, L., Engewald, W., Poppb, P., 1997. Determination of chloroethers in aqueous samples using solid-phase microextraction. Acta Hydrochim. Hydrobiol. 25, 329—incorporated herein by reference in its entirety]. As a result, poor precision and low recoveries were reported [USEPA 1980. United States Environmental Protection Agency, Office of Water Regulations and Standards Criteria and Standards Division Washington D.C. 20460 440/5-80-050 October 1980—incorporated herein by reference in its entirety].

Over the years, different analytical methods have been developed for the determination of haloethers, such as, liquid phase microextraction (LPME), hollow fiber LPME (HF-LPME) and single drop microextraction (SDME) (Zheo et al., 2002), Solid-phase microextraction (SPME) [He, Y., Lee, H. K., 1997. Liquid-Phase Microextraction in a Single Drop of Organic Solvent by Using a Conventional Microsyringe. Anal. Chem. 69, 46; Wang, Y., Kwok, Y. C., He, Y., Lee, H. K., 1998. Application of dynamic liquid-phase microextraction to the analysis of chlorobenzenes in water by using a conventional microsyringe. Anal. Chem. 70, 461; Chiang, S., Huang, D., 2007. Determination of haloethers in water with dynamic hollow fiber liquid-phase microextraction using GC-FID and GC-ECD. Talanta 71, 882-886; Shen, G., Lee, H. K., 2002. Hollow fiber-protected liquid-phase microextraction of triazine herbicides. Anal. Chem. 74, 64; —each incorporated herein by reference in its entirety]. Among these methods, SPME is a solvent-free microextraction technique which combines sampling, sample clean-up and pre-concentration into a single step [Ouyang, G., Vuckovic, D., Pawliszyn, J., 2011. Nondestructive Sampling of Living Systems Using in Vivo Solid-Phase Microextraction. Chem. Rev., 111, 2784; Zeng, J. B., Zou, J., Song, X. H., Chen, J. M., Ji, J. J., Wang, B., Wang, Y. R., Ha, J. H., Chen, X., 2011. A new strategy for basic drug extraction in aqueous medium using electrochemically enhanced solid-phase microextraction. J. Chromatogr. A 1218, 191—each incorporated herein by reference in its entirety].

Although SPME typically involves a relatively straightforward, single-step extraction procedure, SPME fiber capacity is low and not suitable for large volume samples. In light of this deficiency, as well as the shortcomings of other methods as set forth above, the present disclosure provides a simple and safe method for determining the concentration of haloether compounds in an aqueous sample that exhibits excellent analyte recovery at both low and high background matrices.

BRIEF SUMMARY OF THE INVENTION

A method for detecting and quantifying one or more haloether compounds in an aqueous sample is provided in the present disclosure. In one embodiment of the method, a flow state is induced to the aqueous sample to form a flowing aqueous sample. A fiber and an electrode are immersed in the flowing aqueous sample. The one or more haloether compounds present in the flowing aqueous sample are electrophoretically dehalogenated to form a halide ion mixture. The halide ion mixture is contacted with the fiber to absorb a halide ion from halide mixture onto the fiber, where a negative voltage is applied to the fiber and a positive voltage is applied to the electrode during the electrophoretically dehalogenating and the contacting. The halide ion is then desorbed from the fiber in a gas chromatograph. The halide ion is detected with a mass spectrometer and their concentrations are determined.

In certain embodiments, the flowing aqueous sample has a flow rate of 10-100 mL min$^{-1}$.

In some embodiments, the fiber is selected from the group consisting of a polydimethylsiloxane (PDMS) fiber, a polyacrylate (PA) fiber, a carbonwax/divinylbenzene (CW/DVB) fiber, a polydimethylsiloxane/divinylbenzene (PDMS/DVB) fiber, a carboxen/polydimethylsiloxane (CAR/PDMS) fiber, a divinylbenzene/carboxen/polydimethylsiloxane (DVB/CAR/PDMS) fiber, a carbowax-polyethylene glycol (CW/PEG) fiber and a carbowax-templated resin (TPR) fiber, In one embodiment, in the fiber has a thickness of 30-85 μm.

In one or more embodiments, the electrode is made of at least one material selected from the group consisting of palladium, platinum, gold, silver, iridium, rhodium, graphite and an intrinsically conducting polymer.

In one embodiment, the immersing is carried out for 5-15 min at 20-40° C.

In one embodiment, the negative voltage applied is −50 V to −10 V and the positive voltage applied is +10 V to +50 V.

In at least embodiment, the aqueous sample has a volume of 25-200 mL.

In certain embodiments, the one or more haloether compounds are present in the aqueous sample at a concentration of 0.05-200 μg L$^{-1}$.

In one embodiment, the desorbing is carried out at 250-300° C. for 2-10 min.

In some embodiments, the one or more haloether compounds is selected from the group consisting of a chlorophenyl phenyl ether, a dichlorophenyl phenyl ether, a polychlorophenyl phenyl ether, a bromophenyl phenyl ether, a dibromophenyl phenyl ether, and a polybromophenyl phenyl ether.

In some embodiments, the one or more haloether compounds is selected from the group consisting of a chlorophenyl phenyl ether and a bromophenyl phenyl ether.

In one embodiment, during the detecting and the determining, the chlorophenyl phenyl ether has a retention time of 17.5-18.0 min.

In one embodiment, during the detecting and the determining, the bromophenyl phenyl ether has a retention time of 20.0-20.5 min.

In some embodiments, the chlorophenyl phenyl ether and the bromophenyl phenyl ether are detected based on mass-to-charge ratios of 205-210 and 245-255, respectively.

In certain embodiments, the method has a linearity range of 0.5-100 μg L$^{-1}$.

In certain embodiments, the method has a relative standard deviation of 1.2-8.0% for each of the chlorophenyl phenyl ether and the bromophenyl phenyl ether.

In some embodiments, the aqueous sample immersed in the fiber and the electrode has a salt concentration of 2-35%.

In some embodiments, the method comprises mixing one or more acids with the aqueous sample to adjust the pH of the aqueous sample to pH 2 to pH 7.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
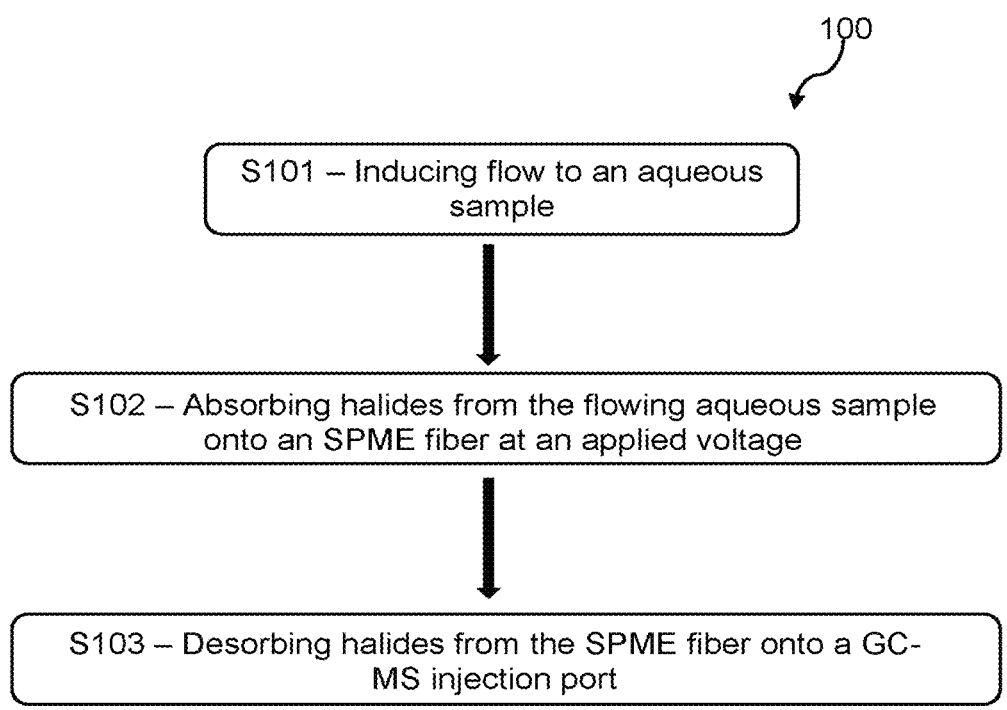
FIG. 1 is a flowchart illustrating an embodiment of the method for detecting and quantifying one or more haloether compounds in an aqueous sample.

Referring now to the drawings, wherein like reference numerals designate identical or corresponding parts throughout the several views.

The method for detecting and quantifying contamination of one or more haloether compounds in an aqueous sample according to the present disclosure involves extraction of the haloether compounds and/or dehalogenates derived therefrom from a flowing aqueous sample with a solid-phase microextraction (SPME) fiber in the presence of an applied electric potential. The extracted halide ions from dehalogenated haloether compounds are then analyzed by gas chromatography-mass spectrometry.

As used herein, "haloethers" are compounds which containing an ether moiety (R—O—R) and one or more halogen atoms attached to the aryl or alkyl groups. Examples of haloethers that may be extracted and detected by the method of the present disclosure include but are not limited to bis(chloromethyl) ether, bis(2-chloroethyl) ether, 2-chloroethyl vinyl ether, bis(2-chloroisopropyl) ether, bis(2-chloroethoxy)methane, monochlorophenyl phenyl ether (2-, 3-, 4- or 5-chlorophenyl phenyl ether), monobromophenyl phenyl ethers (2-, 3-, 4- or 5-bromophenyl phenyl ether), dichlorophenyl phenyl ethers (bis(4-chloro)-, 2,4-, 2,6-, 3,5- dichlorophenyl phenyl ether), polychlorophenyl phenyl ethers (tri-, tetra, penta-, hexa- hepta-, octa- nona- and deca-), dibromophenyl phenyl ethers, polybromophenyl phenyl ethers (tri-, tetra, penta-, hexa- hepta-, octa- nona- and deca-), 2,4,4'-trichloro-2-hydroxy-diphenyl ether, monochlorophenyl methyl ethers, dichlorophenyl methyl ethers, polychlorophenyl methyl ethers, monobromophenyl methyl ethers, dibromophenyl methyl ethers and polybromophenyl methyl ethers. In certain embodiments, haloether compounds that can be sampled and analyzed by the method provided herein are those containing at least one phenyl group, such as but not limited to mono-, di- or polychlorophenyl phenyl ethers; mono-, di- or polybromophenyl phenyl ethers; and mono-, di- or polybromophenyl methyl ethers; mono-, di- or polybromophenyl methyl ethers. Preferably, these haloethers are diphenyl ethers such as but not limited to mono-, di- or polychlorophenyl phenyl ethers and mono-, di- or polybromophenyl phenyl ethers. More preferably, the haloethers that are extracted and analyzed by the method are monochlorophenyl ethers and monobromophenyl ethers. Most preferably, the haloethers are 4-chlorophenyl phenyl ether and 4-bromophenyl phenyl ether.

As used herein, an "aqueous sample" is a sample in liquid form where water is the base solvent. The aqueous sample may be freshwater (naturally occurring water on the earth surface like ice sheets, ice caps, glaciers, icebergs, bogs, ponds, lakes, rivers, streams, seas and oceans), groundwater in aquifers and underground streams, potable water (including tap water and bottled water), processed water (e.g. by filtration, sedimentation, desalination, distillation, biological processes such as slow sand filters and biologically active carbon, chemical processes such as flocculation, agglomeration and chlorination, use of electromagnetic radiation such as ultraviolet light), wastewater (including domestic and industrial effluent water), or mixtures thereof. The aqueous sample has a haloether concentration of 0-250 μg L$^{-1}$, preferably 0.05-200 μg L$^{-1}$, more preferably 0.5-100 μg L$^{-1}$. In one aspect, the method provided in the present disclosure is especially designed to handle large volume samples. Accordingly the aqueous sample may have a volume of up to 250 mL, preferably 25-200 mL, more preferably 50-150 mL, even more preferably 100-125 mL. In one embodiment the aqueous sample has a volume of 100 mL.

A flowchart illustrating an embodiment of the flow assisted, electrically enhanced solid-phase microextraction/gas chromatography-mass spectrometry method for detecting and quantifying one or more haloether compounds in an aqueous sample is given in FIG. 1. Method 100 begins at step S101 where an aqueous sample in a container, which may or may not contain haloether compounds, is mechanically or electrically pumped to artificially induce a flow rate to the aqueous sample, optionally in a predetermined direction. Any pump operating via energy sources such as manual operation, electricity, engine, thermal energy, wind or solar power may be used to induce the flow rate. The pump may be a part of a microextraction system and examples thereof include but are not limited to a gear pump, screw pump, progressing cavity pump, roots-type pump, peristaltic pump, triplex-style plunger pump, compressed-air-powered double diaphragm pump, rope pump, hydraulic ram pump, radial-flow pump, axial-flow pump, mixed-flow pump, eductor-get pump, gravity pump, steam pump and valveless pump. In one embodiment, the pump used to induce flow to the aqueous sample is a peristaltic pump. The flow rate of the aqueous sample is maintained at 10-100 mL min$^{-1}$, preferably 30-80 mL min$^{-1}$, more preferably 40-60 mL min$^{-1}$. In one embodiment, the aqueous sample has a flow rate of 50 mL min$^{-1}$. Applying flow to the aqueous sample the absorptivity (absorption rate and amount of halide ions from dehalogenated haloether compounds onto an SPME fiber) by up to 10 times compared to the static mode, preferably 2-8 times, more preferably 3-6 times.

The microextraction system includes an extraction vial that is connected to the sample container via an input tube and an output tube. The flowing aqueous sample is transported in the predetermined direction, via the input tube, into the extraction vial and is then returned to the sample container via the output tube. A solid-phase microextraction (SPME) fiber and an electrode are inserted into the extraction vial so that at step S102, when the extraction vial is filled with the flowing aqueous sample, the SPME fiber and the electrode are immersed in the sample haloether compounds are absorbed onto the fiber. The absorption proceeds for 2-45 min, preferably 3-30 min, more preferably 5-15 min, even more preferably 7-12 min, most preferably 8-10 min.

The SPME fiber which is optionally coated with a liquid polymer, a solid sorbent or both as an extracting phase that may be non-polar, polar or bipolar. The SPME fiber may be selected from a polydimethylsiloxane (PDMS) fiber, a polyacrylate (PA) fiber, a carbonwax/divinylbenzene (CW/DVB) fiber, a polydimethylsiloxane/divinylbenzene (PDMS/DVB) fiber, a carboxen/polydimethylsiloxane (CAR/PDMS) fiber, a divinylbenzene/carboxen/polydimethylsiloxane (DVB/CAR/PDMS) fiber, a carbowax-polyethylene glycol (CW/PEG) fiber and a carbowax-templated resin (TPR) fiber. The optional extracting phase coating of the SPME fiber has a thickness of 5-100 μm, preferably 30-85 μm. In some embodiments, the SPME fiber is a PDMS fiber, which is non-polar and has a coating film thickness of 30-50 μm, a CW/DVB fiber with a film thickness of 50-65 μm or a PA fiber with a film thickness of 75-85 μm. In one embodiment, the SPME fiber is a PDMS fiber with a 30-μm coating film.

The SPME fiber and the aforementioned electrode are electrically connected to a power source, and are configured to function as a cathode and an anode, respectively, that contact the flowing aqueous sample in the extraction vial during absorption of halides from dehalogenated haloether compounds onto the SPME fiber at step S102. The electrode is made of a conductive material that is inert to dehalogenation of the haloether compounds and absorption of the halides to the SPME fiber, and is preferably a noble metal such as palladium, platinum, gold, silver, iridium and rhodium. In one embodiment, the electrode used the anode is a platinum electrode. In an alternative embodiment, a graphite electrode is used. In yet another embodiment, the electrode is made of one or more intrinsically conducting polymers (e.g. polyanilines, polypyrroles, poly(3,4-ethylenedioxythiophene), copolymers or mixtures thereof).

Still referring to step S102, a negative voltage is applied onto the SPME fiber while a positive voltage is applied onto the electrode, each voltage ranging from ±5-100 V, preferably ±10-50 V, more preferably ±10-30 V). In one embodiment, −15 V is applied onto the SPME fiber while +15 V is applied onto the electrode. The application of electric potentials to the SPME fiber and the electrode, which are both immersed in the flowing aqueous sample in the extraction vial serves at least two purposes. Firstly, haloether compounds in the aqueous sample are electrophoretically dehalogenated to release halide ions. Additionally, applying a negative potential imparts a negative charge to the SPME fiber and/or the SPME fiber coating, which enhances the extraction of dehalogenated ions of the targeted haloether compounds by 2-5 times via electrophoresis and complementary charge interaction and absorption thereof onto the SPME fiber.

The absorption is preferably carried at an ambient temperature ranging from 20-26° C. However, due to the applied electric potential, the absorption temperature may be increased to up to 40° C., for example, 25-40° C., preferably 30-35° C.

After the absorption, at step S103, the SPME fiber is removed from the extraction vial and placed inside the injection port of a gas chromatograph that is coupled to a mass spectrometer, to thermally desorb the halide analyte mixture thermally desorbed at 200-350° C., preferably 250-300° C. for 2-10 min, preferably 2-5 min. In one embodiment, the SPME fiber is desorbed at 290° C. for 3 min.

Following the desorption, the analyte mixture is separated into individual halide ions by a capillary column of the gas chromatograph. Specifically, the difference in chemical properties among different halide ions in the analyte mixture and their relative affinities for the stationary phase of the capillary column will promote separation of the ions as the analyte mixture travels the length of the column, with pure helium flowing at 1.0-1.5 mL min$^{-1}$ as the carrier gas for the analyte mixture. The halides are retained by the column and then elute from the column at different retention times, which allows the downstream mass to capture, ionize, accelerate, deflect and detect the halide ions separately. For chlorophenyl phenyl ether and bromophenyl phenyl ether, the retention times are for example, 17.5-18.0 min and 20.0-20.5 min, respectively. The detection mechanism of the mass spectrometer is to break each halide ion into ionized fragments and detect these fragments using their mass-to-charge ratio. For chlorophenyl phenyl ether and bromophenyl phenyl ether, their mass-to-charge ratios are 205-210 and 245-255, respectively. The mass spectrometer used herein is a single, non-tandem spectrometer involving a single selection step. Hence, based on the detection of the halide ions, the concentrations of individual haloether compounds in the aqueous sample can be determined.

In certain embodiments, the aqueous sample is pre-conditioned prior to the SPME extraction to increase extraction efficiency, by salt addition, pH adjustment, or both. Salts such as sodium chloride and salts of other alkali and alkaline earth metal (e.g. potassium or magnesium) may be used alone or in combination to increase the ionic strength for the aqueous sample to up to 35% (i.e. 35 g of salt per liter of sample), preferably 2-35%, more preferably 3-25%, even more preferably 5-15%. In one embodiment the aqueous sample contains 10% sodium chloride. The pH of the sample may be adjusted with an acid (e.g. hydrochloric acid, sulfuric acid, nitric acid, acetic acid, etc.) so that the sample has a pH value of 2 to 7, preferably 2 to 6, more preferably 2 to 4. In one embodiment, the pH of an aqueous sample, with acid pH adjustment, is 2. Without pH adjustment, the aqueous sample can have a pH of up to 10, for example, pH 5.5 to 10. In one embodiment, the aqueous sample, without pH adjustment, has a pH of 5.7.

Embodiments of the present disclosure include methods for evaluating the analytical performance of the flow assisted, electrically enhanced solid-phase microextraction/gas chromatography-mass spectrometry method set forth herein. Specifically, qualitative parameters of the method such as linear range, repeatability, and limits of detection are determined for chlorophenyl phenyl ether (CPPE) and bromophenyl phenyl ether (BPPE). The method exhibits excellent linearity over a concentration range of 0.5-100 μg L$^{-1}$ for these two haloether compounds ($R^2$>0.98). The limits of detection (LODs) for chlorophenyl phenyl ether and bromophenyl phenyl ether, based on a signal-to-noise (SIN) ratio of 3, are preferably 0.08-0.10 μg L$^{-1}$, specifically 0.085 and 0.093 μg L$^{-1}$, respectively. The relative standard deviation of the calibrations, which reflect reproducibility of the method, are preferably between 1.2 and 8.0% for both chlorophenyl phenyl ether and bromophenyl phenyl ether.

The effect of sample background matrix on the extraction efficiency may be determined by further spiking a haloether-containing aqueous sample (CPPE and BPPE) with a low concentration and a high concentration of a CPPE and BPPE equimolar mixture. In one embodiment, the aqueous sample contains 100-120 μg L$^{-1}$ of CPPE and BPPE, but is further spiked with 5-10 μg L$^{-1}$ of the haloether mixture (low concentration) and 30-50 μg L$^{-1}$ of the mixture (high concentration). In one embodiment, the unspiked aqueous sample has a haloether concentration of 100 μg L$^{-1}$ and the spiked samples contain 105 μg L$^{-1}$ and 130 μg L$^{-1}$ of the haloethers. At a sample concentration of 100-120 μg L$^{-1}$ of the two diphenyl halothers, the method has an extraction recovery of 1-10%, preferably 2-7%, more preferably 2.5-5.5%. At 105-110 µg L$^{-1}$, the extraction recovery is 5-10%, preferably 6-10%, more preferably 7-10%. At a high haloether concentration of 130-150 µg L$^{-1}$, the extraction recovery increases to 25-40%, preferably 25-35%, more preferably 30-35%. Thus, a lack of sample background matrix interference is observed for the extraction method described herein.

EXAMPLES

The following examples are included herein to further illustrate protocols for setting up an embodiment of a system for solid phase microextraction of haloethers, an embodiment of a gas chromatography-mass spectrometry analysis system and protocols for characterizing the haloether detection and quantification method. It should be made clear that these examples are included strictly for illustrative purposes only, and are not intended to limit the scope of the invention.

In these examples, a flow assisted electro-enhanced solid-phase microextraction (FA-EE-SPME) method was developed for the determination of haloethers. Different fibers were exposed in to a 100 mL sample via direct immersion mode for 10 min with an applied potential (−15V) to extract 4-chlorophenyl phenyl ether (CPPE) and 4-bromophenyl phenyl ether (BPPE). After extraction, the SPME fiber was desorbed in the injector port of gas chromatography-mass spectrometry (GC-MS). Quantification was carried out over a concentration range of 0.5 to 100 µg L$^{-1}$ and good linearity was obtained with detection limits of 0.085 and 0.093 µg L$^{-1}$ respectively. The relative standard deviations of the calibrations were evaluated and were in the range between 1.2 and 8.0%. Application of FA-EE-SPME was tested for various water samples collected from Eastern Province of Saudi Arabia and the method performance was compared with reported literature values. Comparatively, the FA-EE-SPME gave higher analyte enhancement for large volume samples. The developed extraction procedure provides a convenient and efficient method for assay at ultra-trace levels. Moreover, the proposed FA-EE-SPME is suitable for on-site applications.

Example 1

Chemicals and Materials

Figure 2A:
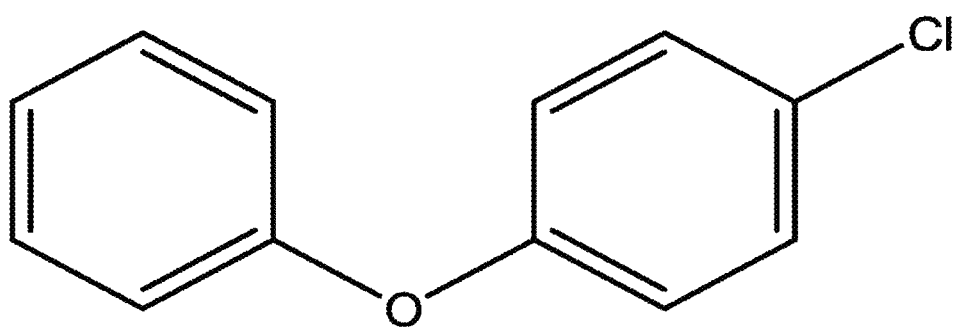
FIG. 2A shows the chemical structure of 4-chlorophenyl phenyl ether (CPPE).
Figure 2B:
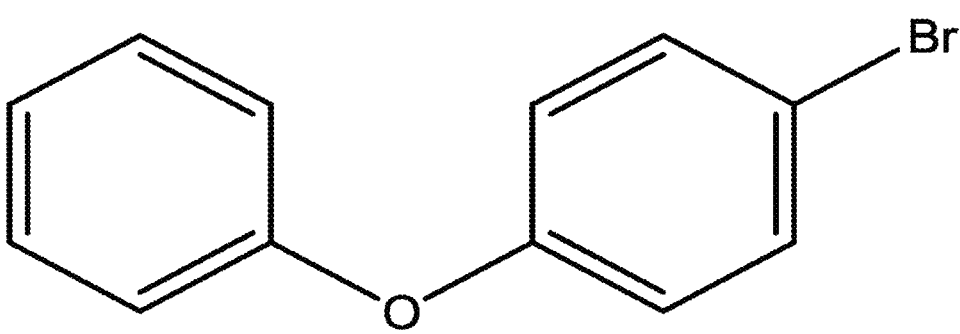
FIG. 2B shows the chemical structure of 4-bromophenyl phenyl ether (BPPE).

A mixture of haloether standards were purchased from Supelco (Bellefonte, Pa., USA). This mixture, containing 4-chlorophenyl phenyl ether (CPPE) and 4-bromophenyl phenyl ether (BPPE) at 2000 µg mL$^{-1}$ each compound, was prepared in methanol. Preparing working standard solutions daily by appropriate dilution of stock solution of haloethers in same solvent (see FIGS. 2A and 2B for molecular structures for CPPE and BPPE). Analytical grade solvents were obtained from Supelco (Bellefonte, Pa., USA). Double deionized water was obtained from a Milli-Q system (Millipore, Bedford, Mass., USA). Sodium hydroxide, sulfuric acid and sodium chloride were purchased (Merck, Darmstadt, Germany). All used glassware was washed with concentrated hydrochloric acid and rinsed with deionized water and acetone then dried in oven at 100° C. for 1 h. Three commercially available fibers were tested to extract haloethers. Polydimethylsiloxane (PDMS, 30 µm), carbowax/divinylbenzene (CW/DVB, 65 µm) and polyacrylate (PA, 85 µm) coated fibers were purchased from Supelco (Supelco, Bellefonte, Pa., USA) and used without any modifications. The platinum wire electrode that was used to complete the electrical circuit was purchased (CHI115, CH Instruments Inc, USA).

Example 2

Aqueous Samples

Different brands of drinking bottled water samples were purchased from local market in (Khobar-Saudi Arabia) also drinking water from KFUPM treatment plan and tap water sample collected from two different sources (main campus of KFUPM and Dammam housing) were tested without any further physical pre-treatment such as, filtration.

Example 3

Figure 3:
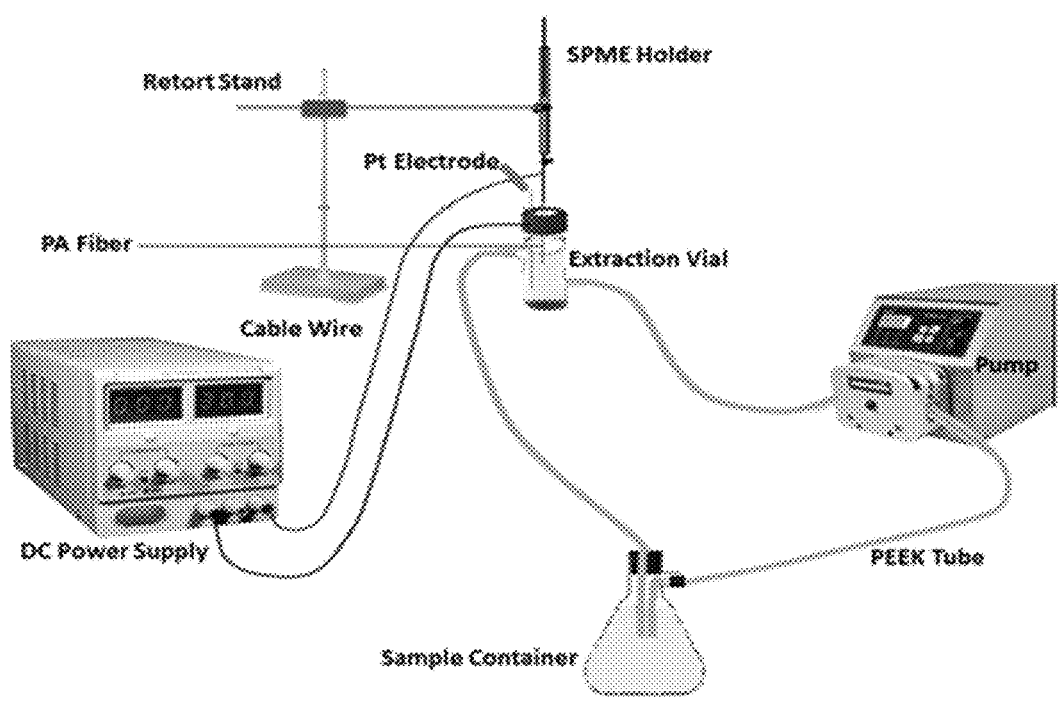
FIG. 3 is a schematic diagram of a flow assisted electro-enhanced solid phase microextraction system according to one embodiment.

Flow Assisted, Electro-Enhanced Solid Phase Microextraction (FA-EE-SPME) of Haloethers A 100 mL aqueous sample spiked with haloethers containing was placed in a 125 mL flask connected by two polyetheretherketone (PEEK) tubes. Through the input tube, the aqueous sample passes through an electrical pump to the extraction vial while the output tube carries the sample back to the same flask. A 20 mL modified auto-sampler extraction glass vial was connected to the tubes. An SPME fiber and an inert wire (platinum) were inserted in the sample solution. Both the Pt wire and SPME holder were connected via cable wires to the DC power supply. The SPME fiber was immersed in the sample solution. A negative voltage (−15 V) was applied to the SPME fiber and a positive (+15 V) potential was applied to the platinum electrode as shown in the FIG. 3. Then the sample was running at 50 mL min$^{-1}$ flow rate for 10 min. After the extraction, the fiber was thermally desorbed in the GC-MS injection port for 3 min at 290° C.

Example 4

Gas Chromatography-Mass Spectrometry Analysis of Haloethers

Analyses were carried out using a gas chromatograph (Agilent technologies, 6890N GC) coupled with a mass spectrometer (Agilent technologies, 5975B MSD). An HP-1 methyl siloxan column (Agilent 19091Z-213; 30 m×320 µm I.D.×1 µm thickness) was used. High purity helium (>99.999%) was used as a carrier gas and the samples were analyzed in a constant flow at 1.2 mL min$^{-1}$. The fiber was thermally desorbed in the GC-MS injection port for 3 min at 290° C. The temperature program used for the analyses was as follows: the initial temperature was 40° C. held 1 min which was then increased to 118° C. at 10° C. min$^{-1}$ and held for 3 min, then to 190° C. at 15° C. min$^{-1}$ and held for 7 min. The total run time was 21.6 min. The injection port, ion source and interface temperatures were 280° C., 230° C., and 250° C., respectively. For qualitative determinations, the mass spectrometer was operated in full-scan mode from m/z (mass-to-charge ratio) values of 50 to 550 and selective ion monitoring mode was used for the quantitative quantification of the analytes.

Example 5

Effect of Absorption Time of SPME Fiber

Figure 4:
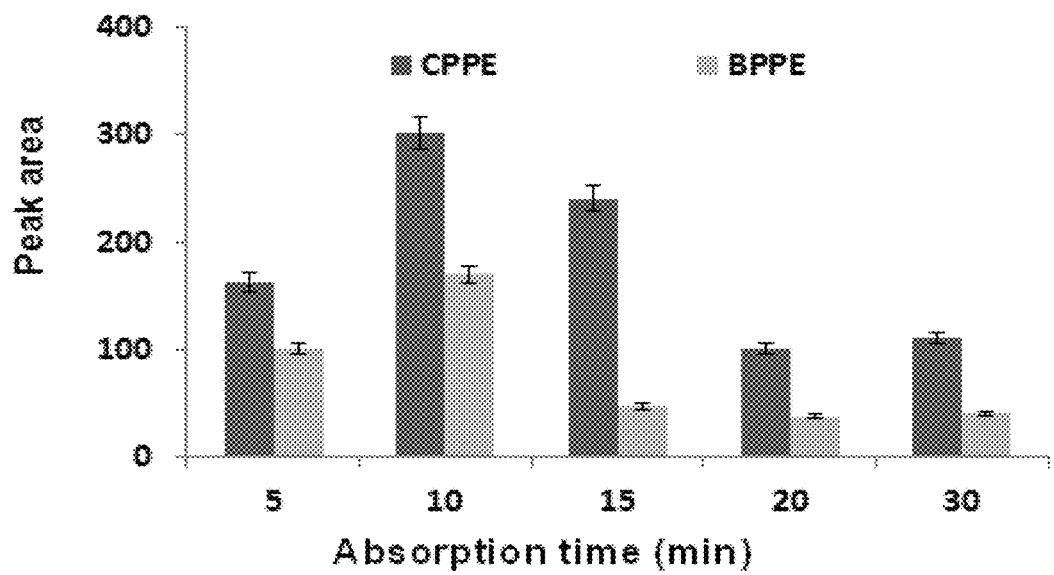
FIG. 4 is a bar graph showing effects of absorption on extraction of CPPE and BPPE (100 mL of sample spiked by 100 μg L$^{-1}$ haloethers, flow rate 50 mL min$^{-1}$, desorption time 3 min, pH 5.7).

The effect of absorption time of SPME fiber was studied between 5 and 30 min extraction time. FIG. 4 shows the GC-MS peak areas of haloethers and extraction time. Peak areas were increased up to 10 min and then slightly decreased. Sampling agitation and stronger flow of water sample may increase the extraction profile quickly to reach equilibrium with the SPME fiber and then analytes desorbed slowly in the sample matrix.

Example 6

Effect of Pump Flow Rate

Figure 5:
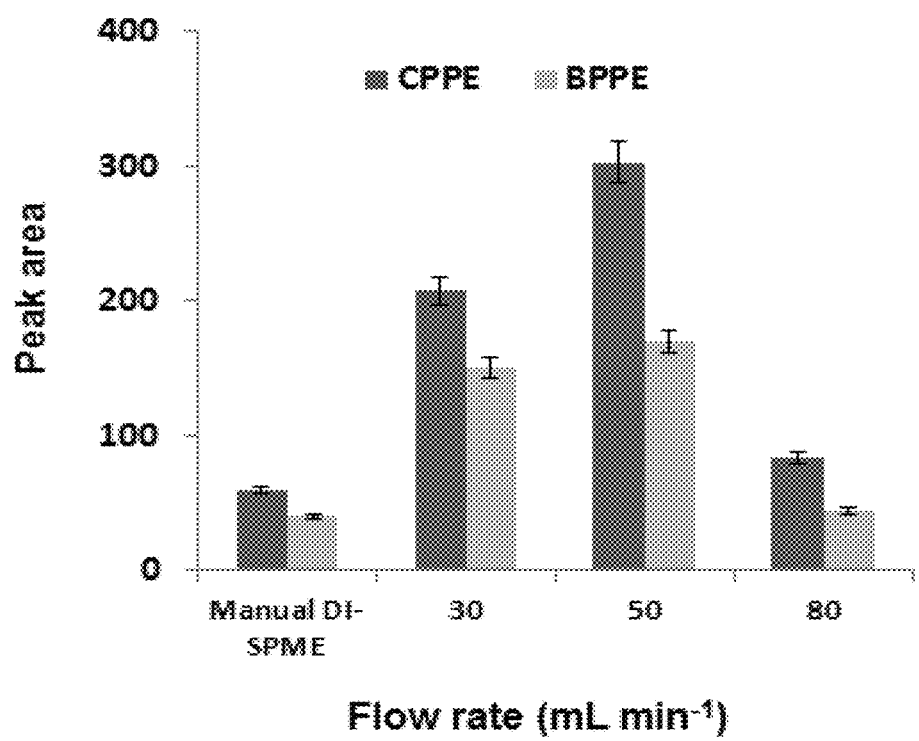
FIG. 5 is a bar graph showing effects of sample flow rate on extraction of CPPE and BPPE at 10 min absorption time and the same conditions described above.

To investigate the effect of sample flow rate on the SPME extraction, samples were pumped using a peristaltic pump in the range between 0 and 80 mL min$^{-1}$. FIG. 5 shows the influence of sample flow over static mode (0 flow rate). As can be seen in FIG. 5, the signal increased upon changing the flow rate till 50 mL min$^{-1}$ and then started decreasing after that. A flow rate of 50 mL min$^{-1}$ gave higher peak areas compared to other flow rates. It is inferred that the concentration of adsorbed analyte at SPME surface decreased at high pump flow rate due to strong vibration of SPME fiber leads to desorption of analytes back to sample matrix.

Example 7

Effect of Ionic Strength

Figure 6:
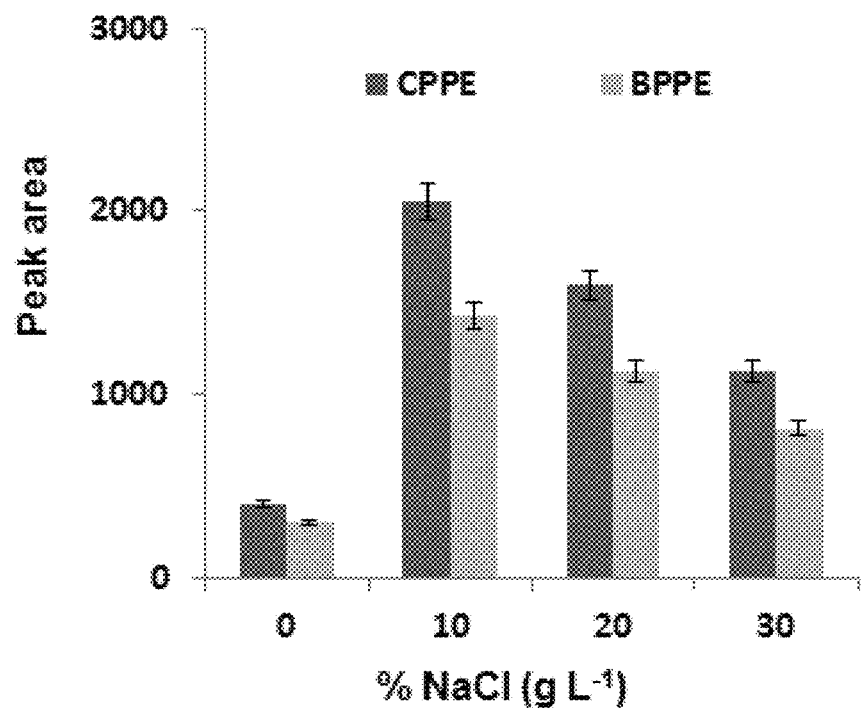
FIG. 6 is a bar graph showing effects of salt addition (10% NaCl) on extraction of CPPE and BPPE at the same conditions described FIG. 5.

FIG. 6 reflects the effect of ionic strength on the extraction efficiency of haloethers over the concentrations of added NaCl range (0-35%, (w/v)), As can be seen the highest extraction efficiency for all haloethers was at salt concentration 10% (w/v). The response started decreasing for solutions containing higher than 10% (w/v) salt. The effect of NaCl on the extraction of haloethers could be due to two factors. The first factor is salting-out effect, which decreases the solubility of the analytes, and thus increases the absorption. Secondly, dissolving salt in the solution may change the physical properties of the static aqueous layer on the fiber, and thereby reduce the rate of diffusion of the analyte through the static aqueous layer to the fiber [Fawell, J. K., Hunt, S., 1988. Environmental Toxicology: Organic Pollutants, Wiley, New York, (Chapter 9); Zeng, J. B., Zou, J., Song, X. H., Chen, J. M., Ji, J. J., Wang, B., Wang, Y. R., Ha, J. H., Chen, X., 2011. A new strategy for basic drug extraction in aqueous medium using electrochemically enhanced solid-phase microextraction. J. Chromatogr. A 1218, 191—each incorporated herein by reference in its entirety].

Example 8

Sample pH

Figure 7:
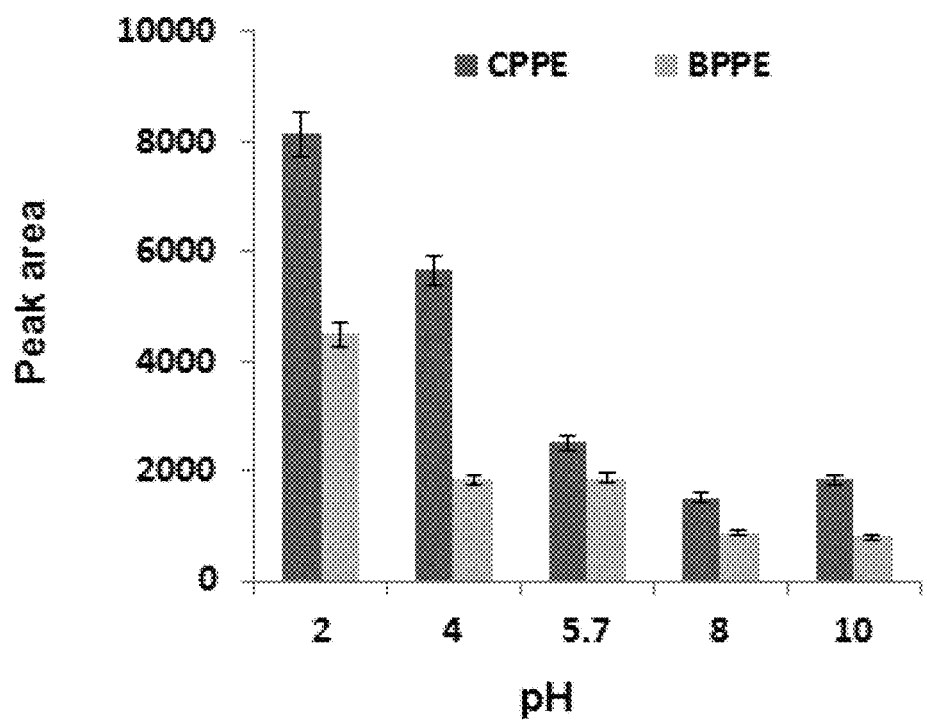
FIG. 7 is a bar graph showing effects of sample pH on extraction of CPPE and BPPE at the same conditions described for FIG. 5.

To find out the best detection medium pH, sample pH was examined in the range of (2-10), as shown in FIG. 7. The extraction efficiency gives the best response at pH 2. At alkaline conditions, low efficiency was obtained which could be due to hydrolysis of haloethers.

Example 9

Effect of Applied Voltage on SPME

Figure 8A:
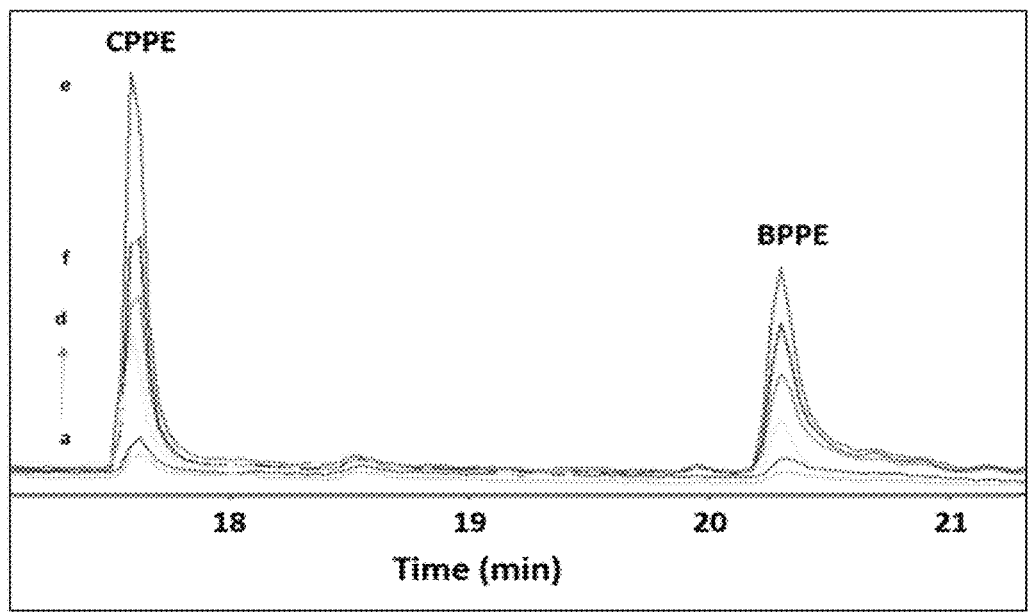
FIG. 8A shows chromatograms of applying different potentials on extraction of CPPE and BPPE: (a)+5.0 V, (b) 0.0 V, (c) −5.0 V, (d) −10.0 V, (e) −15.0 V and (f) −20.0 V.
Figure 8B:
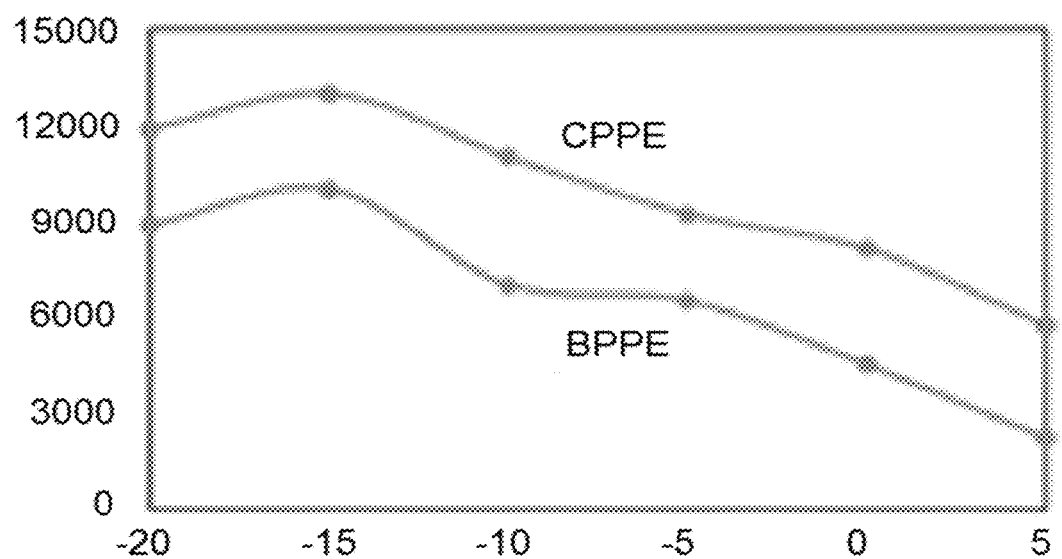
FIG. 8B shows plots of potential versus peak area of target compounds CPPE and BPPE at the same conditions described for FIG. 7.

A substantial enhancement of haloether response is observed when applying different potential. FIGS. 8A and 8B display the effect of different potential on haloethers. Potential values varying from −20 V to +5 V were applied for the SPME method ((a) +5.0 V, (b) 0.0 V, (c) −5.0 V, (d) −10.0 V, (e) −15.0 V and (f) −20.0 V). As expected, negative potential values give better result because the ionic form CPPE and BPPE in the aqueous medium has positive charge. Applying negative potentials made the fiber coating negatively charged and therefore enhanced the extraction of dehalogenated ions of target compound via electrophoresis and complementary charge interaction [Zeng, J. B., Zou, J., Song, X. H., Chen, J. M., Ji, J. J., Wang, B., Wang, Y. R., Ha, J. H., Chen, X., 2011. A new strategy for basic drug extraction in aqueous medium using electrochemically enhanced solid-phase microextraction. J. Chromatogr. A 1218, 191—incorporated herein by reference in its entirety].

Example 10

Effects of SPME Fibers

Figure 9:
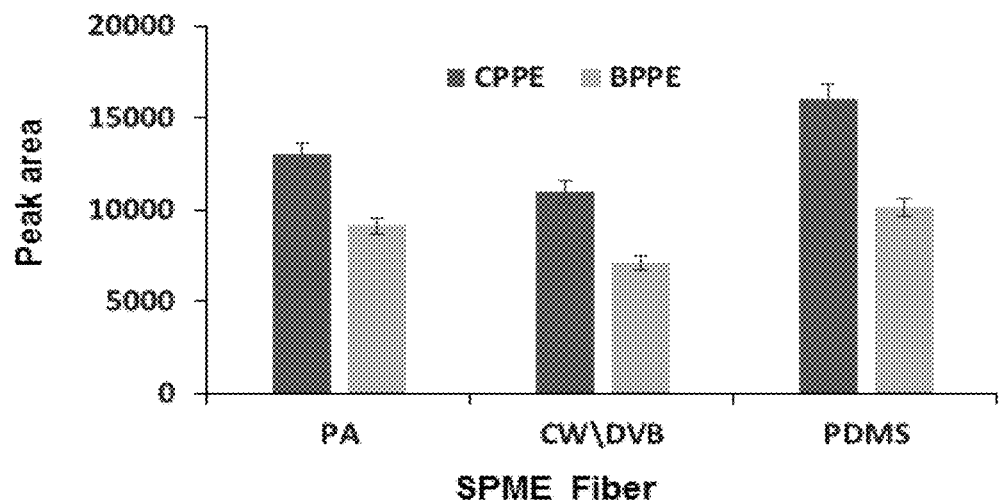
FIG. 9 is a bar graph showing effects of SPME fibers on extraction of CPPE and BPPE (sample pH 2, other conditions as described for FIG. 7).

Three commercially available fibers were tested to extract CPPE and BPPE. PDMS, CW/DVB and PA coated fibers used without any modifications. The fibers were conditioned prior to use according to the instructions provided by the suppliers. FIG. 9 shows the extraction performance and PDMS gives the highest peak areas for both analytes. PDMS fiber shows higher extraction efficiency this could be due to the applied potential plays a major role on the extraction of polar compounds.

Example 11

Analytical Performance of FA-EE-SPME/GC-MS

Figure 10:
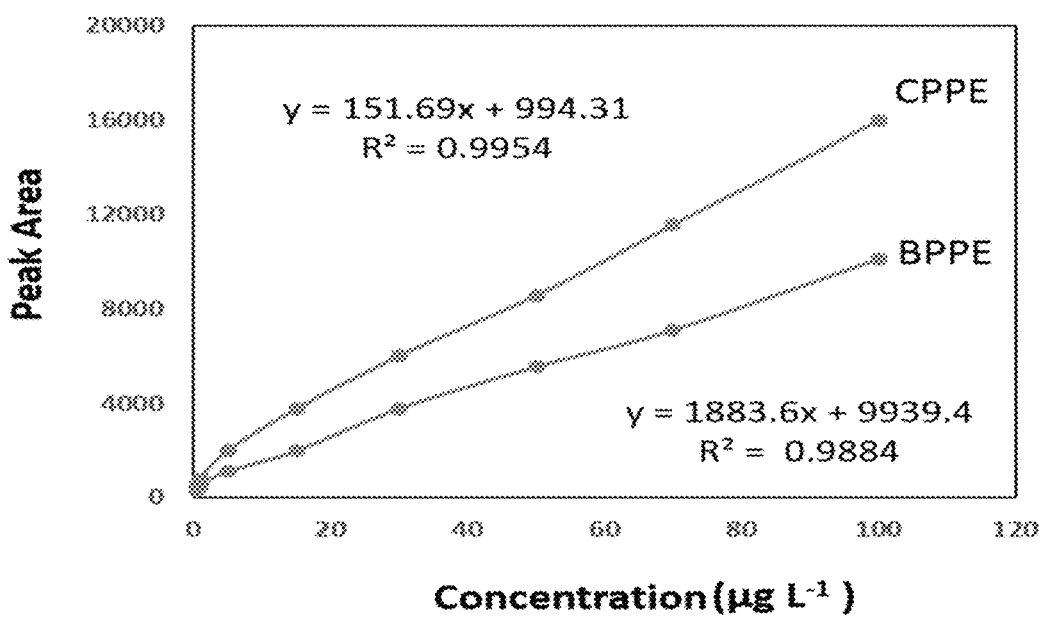
FIG. 10 shows calibration curves for CPPE and BPPE at different concentrations and same conditions as described for FIG. 9.

The analytical performance of the FA-EE-SPME/GC-MS method was assessed by monitoring the dependence of the CPPE and BPPE peak area at a different concentration level of (0.5, 1, 5, 10, 20, 40, 70, 100 μg L$^{-1}$). Quantitative parameters (linear range, repeatability, and limits of detection) were calculated under the following conditions: 100 mL of sample spiked by 100 μg L$^{-1}$ haloethers, sample pH 2, flow rate 50 mL absorption time 10 min, desorption time 3 min. Excellent linearity was observed over the concentration range of 0.5-100 μg L$^{-1}$ for CPPE and BPPE. The LODs, based on a (S/N ratio of 3), were 0.085 and 0.093 μg L$^{-1}$, respectively. FIG. 10 shows the calibration curve for both compounds including related equations and their regression factor (R$^2$). The results confirmed that the FA-EE-SPME/GC-MS method described herein is suitable for trace level analysis of haloethers in water samples. Table 2 shows the retention time and fragment ions of CPPE and BPPE analytes determined by FA-EE-SPME/GC-MS. Table 3 summarizes the main differences between the present method with previously reported works. The developed method showed promising results compared with previously reported. The main advantages of the present method over other microextraction techniques are simple, solvent-free pre-concentration system with high precision and low detection limits.

TABLE 2

Retention time and fragment ions of CPPE and BPPE.

| Analytes | Retention time (min) | Fragment (m/z) |
|---|---|---|
| CPPE | 17.88 | 206[a], 204, 141, 169, 128 |
| BPPE | 20.45 | 250[a], 248, 168, 154, 141 |

[a]Target ions.

TABLE 3

Comparison of the FA-EE-SPME/GC-MS haloether detection and quantification method of the present disclosure with previously reported methods.

| Analytical technique | Extraction time | LODs for CPPE or BPPE ($\mu g\ L^{-1}$) | Reference |
|---|---|---|---|
| HF[a]-LPME/GC-FID[b] | 30 min | 0.55-0.66 | Jing. S. C., Shang. D. H., 2007. Determination of haloethers in water with dynamic hollow fiber liquid-phase microextraction using GC-FID and GC-ECD. Talanta 71, 882 - incorporated herein by reference in its entirety. |
| HF-LPME/GC-ECD[c] | 30 min | 0.29-0.11 | |
| Method 611 of USEPA LLE | ~2 h | 3.9-2.3 | USEPA 1980. United States Environmental Protection Agency, Office of Water Regulations and Standards Criteria and Standards Division Washington DC 20460 440/5-80-050 October 1980 - incorporated herein by reference in its entirety. |
| FA-EE-SPME/GC-MS | 10 min | 0.085-0.093 | The present disclosure |

[a]Hollow fiber assisted liquid phase microextraction
[b]Flame ionization detector
[c]Electro capture detector Example 12

Water Sample Analysis

Figure 11:
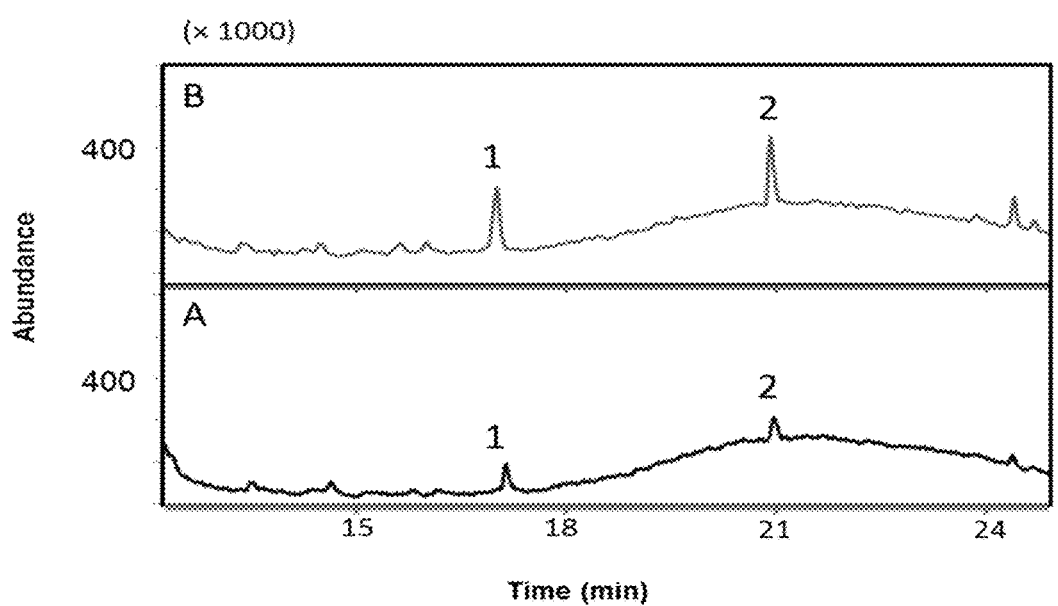
FIG. 11 shows chromatograms of CPPE and BPPE in drinking water samples A (unspiked drinking water) and B (drinking water spiked with 5 μg/L of haloethers).

The FA-EE-SPME/GC-MS method was tested for the detection of haloethers in different water samples. Drinking and tap water samples were subjected to the following conditions of the microextraction: 100 mL of sample spiked by 100 $\mu g\ L^{-1}$ haloethers, sample pH 2, flow rate 50 mL min$^{-1}$, absorption time 10 min, desorption time 3 min. The volume of each water sample was 100 mL. The concentrations of CPPE and BPPE that were detected by this method were shown in Table 4. To assess the matrix effect, real samples were further spiked with 5 $\mu g\ L^{-1}$ and 30 $\mu g\ L^{-1}$ of target analytes and extraction recoveries were calculated as shown in Table 4. FIG. 11 shows the GC-MS chromatograms of unspiked and spiked drinking water samples which clearly indicates that no sample matrix interference for this method. Sample A contains 100 $\mu g\ L^{-1}$ CPPE and BPPE while Sample B contains 100 $\mu g\ L^{-1}$ but is further spiked with 5 $\mu g\ L^{-1}$ of CPPE and BPPE.

TABLE 4

Extraction recoveries of CPPE and BPPE from water samples containing 100 $\mu g\ L^{-1}$ of the haloethers and are further spiked with 5 $\mu g\ L^{-1}$ and 30 $\mu g\ L^{-1}$ of the haloethers

| | CPPE | | | BPPE | | |
|---|---|---|---|---|---|---|
| | 100 $\mu g\ L^{-1}$ | 100 $\mu g\ L^{-1}$ spiked with 5 $\mu g\ L^{-1}$ (105 $\mu g\ L^{-1}$) | 100 $\mu g\ L^{-1}$ spiked with 30 $\mu g\ L^{-1}$ (130 $\mu g\ L^{-1}$) | 100 $\mu g\ L^{-1}$ | 100 $\mu g\ L^{-1}$ spiked with 5 $\mu g\ L^{-1}$ (105 $\mu g\ L^{-1}$) | 100 $\mu g\ L^{-1}$ spiked with 30 $\mu g\ L^{-1}$ (130 $\mu g\ L^{-1}$) |
| KFUPM Tap Water | 4.1 ± 0.67 | 8.3 ± 0.25 | 33.2 ± 0.31 | 5.8 ± 0.45 | 9.8 ± 0.71 | 34.9 ± 0.65 |
| Dammam Tap Water | 5.1 ± 0.77 | 9.9 ± 0.27 | 34.2 ± 0.41 | 5.3 ± 0.36 | 10.0 ± 0.73 | 35.0 ± 0.46 |
| KFUPM Drinking Water | 4.0 ± 0.68 | 8.9 ± 0.58 | 33.1 ± 0.59 | 3.7 ± 0.45 | 7.8 ± 0.46 | 32.8 ± 0,77 |
| Drinking Water (1) | 3.9 ± 0.78 | 7.9 ± 0.48 | 32.1 ± 0.39 | 3.3 ± 0.55 | 7.8 ± 0.36 | 32.8 ± 0.27 |
| Drinking Water (2) | 3.1 ± 0.77 | 7.8 ± 0.35 | 32.8 ± 0.51 | 3.8 ± 0.55 | 8.4 ± 0.79 | 32.9 ± 0.69 |
| Drinking Water (3) | 2.5 ± 0.32 | 7.3 ± 0.12 | 32.1 ± 0.44 | 2.1 ± 0.65 | 7.0 ± 0.81 | 31.9 ± 0.42 |
| Drinking Water (4) | 3.8 ± 0.45 | 8.5 ± 0.39 | 33.0 ± 0.59 | 3.1 ± 0.11 | 8.0 ± 0.66 | 32.5 ± 0.35 |

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for detecting and quantifying one or more haloether compounds in an aqueous sample, comprising:
    inducing a flow state to the aqueous sample to form a flowing aqueous sample;
    immersing a fiber and an electrode into the flowing aqueous sample;
    applying a negative voltage to the fiber and a positive voltage to the electrode while the fiber is in contact with the flowing aqueous sample to adsorb the one or more haloether compounds onto the fiber;
    removing the fiber from the flowing aqueous sample and thermally desorbing the one or more haloether compounds from the fiber in an injection port of a gas chromatograph-mass spectrometer (GC-MS); and
    subjecting the one or more haloether compounds to GC-MS analysis to detect and determine a concentration of the one or more haloether compounds;
    wherein the aqueous sample has a pH of 2; and
    wherein the one or more haloether compounds are selected from the group consisting of a chlorophenyl phenyl ether and a bromophenyl phenyl ether.

2. The method of claim 1, wherein the flowing aqueous sample has a flow rate of 10-100 mL min$^{-1}$.

3. The method of claim 1, wherein the flowing aqueous sample has a flow rate of 40-60 mL min$^{-1}$.

4. The method of claim 1, wherein the fiber is selected from the group consisting of a polydimethylsiloxane (PDMS) fiber, a polyacrylate (PA) fiber, a carbonwax/divinylbenzene (CW/DVB) fiber, a polydimethylsiloxane/divinylbenzene (PDMS/DVB) fiber, a carboxen/polydimethylsiloxane (CAR/PDMS) fiber, a divinylbenzene/carboxen/polydimethylsiloxane (DVB/CAR/PDMS) fiber, a carbowax-polyethylene glycol (CW/PEG) fiber and a carbowax-templated resin (TPR) fiber.

5. The method of claim 1, wherein the fiber is a polydimethylsiloxane (PDMS) fiber.

6. The method of claim 1, wherein the fiber has a thickness of 30-85 µm.

7. The method of claim 1, wherein the electrode is made of at least one material selected from the group consisting of palladium, platinum, gold, silver, iridium, rhodium, graphite and an intrinsically conducting polymer.

8. The method of claim 1, wherein the aqueous sample has a volume of 25-200 mL.

9. The method of claim 1, wherein the one or more haloether compounds are present in the aqueous sample at a concentration of 0.05-200 µg L$^{-1}$.

10. The method of claim 1, wherein the aqueous sample has a salt concentration of 2-35% by weight per volume of the aqueous sample (w/v).

11. The method of claim 1, wherein the immersing is carried out for 5-15 min at 20-40° C.

12. The method of claim 1, wherein the immersing is carried out for 8-10 min at 20-40° C.

13. The method of claim 1, where the negative voltage applied is −50 V to −10 V and the positive voltage applied is +10 V to +50 V.

14. The method of claim 1, wherein the negative voltage applied is −20 V to −15 V and the positive voltage applied is +15 V to +20 V.

15. The method of claim 1, wherein the thermally desorbing is carried out at 250-300° C. for 2-10 min in the injection port of the GC-MS.

16. The method of claim 1, wherein the one or more haloether compounds is the chlorophenyl phenyl ether, which has a retention time of 17.5-18.0 min when subjected to the GC-MS analysis.

17. The method of claim 1, wherein the one or more haloether compounds is the bromophenyl phenyl ether, which has a retention time of 20.0-20.5 min when subjected the GC-MS analysis.

* * * * *